United States Patent [19]

Kurtz et al.

[11] Patent Number: 4,782,060

[45] Date of Patent: Nov. 1, 1988

[54] GEPIRONE FOR ALLEVIATION OF PANIC DISORDERS

[75] Inventors: Neil Kurtz, Weston, Conn.; Roger E. Newton, Evansville, Ind.; Davis L. Temple, Jr., Wallingford, Conn.

[73] Assignee: Bristol-Myers Company, New York, N.Y.

[21] Appl. No.: 79,190

[22] Filed: Jul. 29, 1987

[51] Int. Cl.$^4$ .................. A61K 31/50; A61K 31/495
[52] U.S. Cl. .................................................. 514/252
[58] Field of Search ........................................ 514/252

[56] References Cited

U.S. PATENT DOCUMENTS 4,423,049 12/1983 Temple, Jr. .......................... 544/360
4,634,703 1/1987 Kurtz et al. ......................... 514/252

OTHER PUBLICATIONS

Annual Reports in Medicinal Chemistry: vol. 21, Editor-in-Chief D. M. Bailey, Academic Press, Inc., 1986, pp. 15, 43. (2/3).

D. W. Matuzas, et al., *Archives General Psychiatry*, 40, pp. 220-222 (1983). (4/12).

A. B. Breier, et al., *American Journal of Psychiatry*, 142: 7, pp. 787-796 (1985). (3/18).

D. V. Sheehan, *New England Journal of Medicine*, 307, pp. 156-158 (1982). (4/7).

R. I. Shader, et al., *Journal Clinical Psychopharmacology*, 2/6 Supplement, pp. 2S-26S (1982). (4/9).

*Primary Examiner*—Stanley J. Friedman
*Attorney, Agent, or Firm*—Richard P. Ryan

[57] ABSTRACT

Gepirone and its pharmaceutically acceptable salts are useful in alleviation of panic disorders which can take the form of clinical syndromes comprising, for example, panic attacks, agoraphobia and phobic anxiety.

8 Claims, 1 Drawing Sheet

GEPIRONE FOR ALLEVIATION OF PANIC DISORDERS

FIELD OF THE INVENTION

This invention is concerned with a drug bio-affecting body-treating process which employs the pyrimidine compound 4,4-dimethyl-1-[4-[4-(2-pyrimidinyl)-1-piperazinyl]butyl]-2,6-piperidinedione or a pharmaceutically acceptable acid addition salt thereof.

BACKGROUND OF THE INVENTION

The pyrimidine compound with which the present invention is concerned has the following structural formula

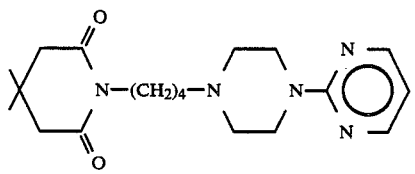

and is known as gepirone. The hydrochloride salt has been referred to in the prior art as MJ 13805-1 and as gepirone hydrochloride. Other acid addition salts thereof are named by combining "gepirone" with the appropriate word to define the acid from which it is prepared as in "gepirone hydrochloride". The latter is the U.S. adopted name (USAN); refer to the "1986 USAN and the USP Dictionary of Drug Names" which is published by the United States Pharmacopeial Convention, Inc.

The synthesis of the compound and the disclosure of its anxiolytic properties are described in the following patents and publications.

1. D. L. Temple, Jr., U.S. Pat. No. 4,423,049, issued Dec. 27, 1983.
2. Annual Reports in Medicinal Chemistry: Volume 21, Editor-in-Chief D. M. Bailey, Academic Press, Inc., 1986, Pages 15, 43.

Gepirone has also been reported to be an anxiolytic agent with antidepressant properties as disclosed in the following representative references.

3. Eison, et al., *Eur. J. Pharmacol.*, III: 389–392 (1985).
4. Eison, et al., *Drugs of the Future*, 10: 456–457 (1985).

The method of the present invention can be distinguished from the above prior art in that it is directed to a distinct patient population characterized by a disease state different from that related to anxiety and anxiety with mixed depression disclosed in this prior art. Support for this distinction is found in reference 5, "The Diagnostic Validity of Anxiety Disorders and Their Relationship to Depressive Illness", by A. B. Boyer, et al. in *Am. J. Psychiatry*, 142: 7, pp. 787–796 (1985).

Although panic disorder is a relatively new diagnosis, the basic diagnostic concepts are well known to those skilled in the art and are clearly differentiated from generalized, persistent anxiety states. The following references are examples of literature reviewing the diagnosis and treatment of panic disorders.

6. D. V. Sheehan, "Panic Attacks and Phobias", *New England J. of Med.*, 307, pp. 156–158 (1982).
7. R. I. Shoder, et al., "Panic Disorders: Current Perspectives", *J. Clin. Psychopharmacology*, 2/6 Supplement, pp. 25–265 (1982).
8. W. Matuzas, et al., "Treatment of Agoraphobia and Panic Attacks", *Arch. Gen. Psychiatry*, 40, pp. 220–222 (1983).

A possibly relevant disclosure is our own earlier invention of U.S. Pat. No. 4,634,703 which issued Jan. 6, 1987 in which another pyrimidine compound, buspirone, was disclosed and claimed as being useful in the treatment of panic disorders. We believe that upon consideration of all applicable prior art that there is no teaching or suggestion that the instant compounds would be useful in alleviation of panic disorder.

SUMMARY OF THE INVENTION

The process of the present invention is intended for the alleviation of panic disorders of which panic attacks, agoraphobia, and phobic anxiety are specific examples. The process essentially involves administration of gepirone, or a pharmaceutically acceptable acid addition salt thereof, to one in need of such treatment. For use in the instant process oral administration of gepirone hydrochloride from about 10 to 60 mg per day in divided doses is anticipated as being the preferred dosage regimen.

DETAILED DESCRIPTION OF THE INVENTION

Figure 1:
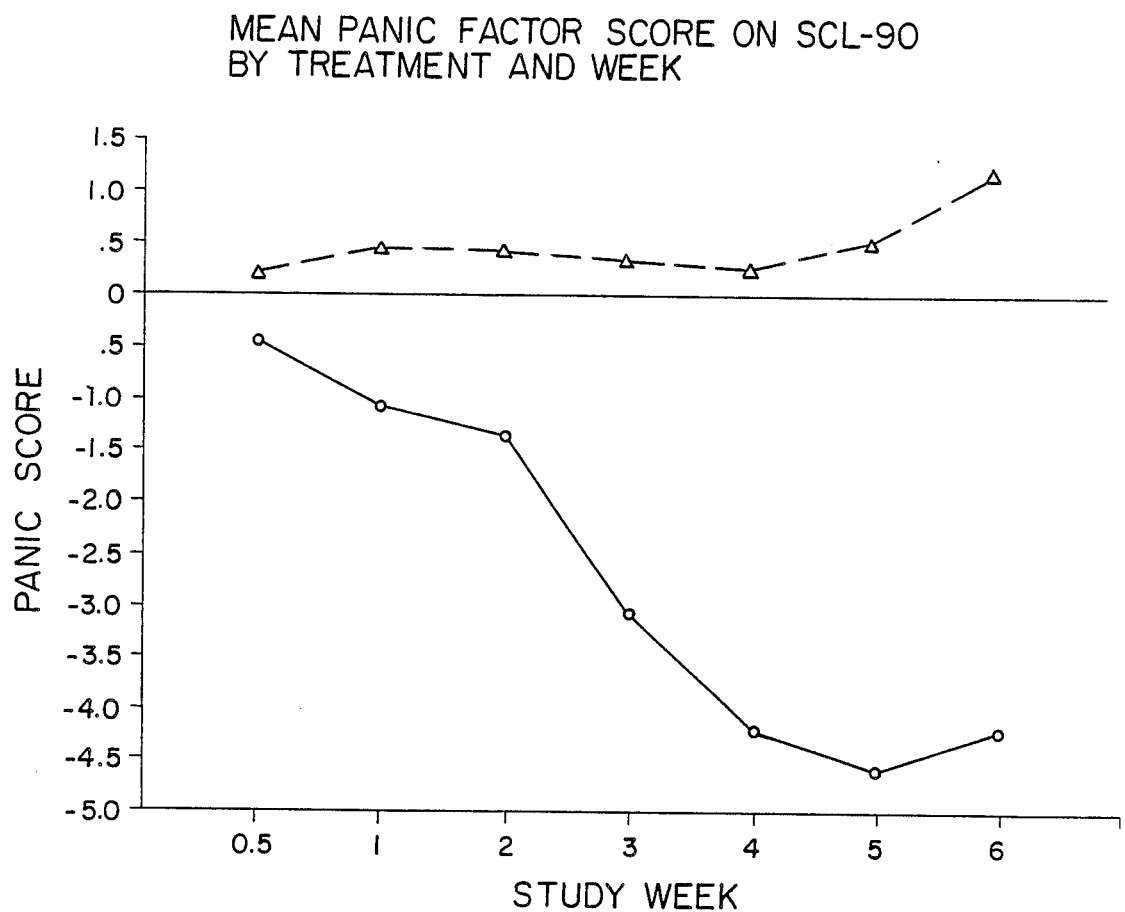
FIG. 1 graphically demonstrates the time course relationship over a six-week treatment period of mean patient changes from base-line values of a panic score for gepirone (solid line) and placebo (broken line) treated patient groups.

Panic disorders are best defined clinically by the frequent occurrence of panic attacks in patients. A panic attack is described as a sudden surge of intense discomfort and/or fear which can occur either spontaneously, seemingly without cause, or can occur as situational episodes. Within 10 minutes of the onset of the panic attack a variety of characteristic symptoms may develop. These symptoms can include shortness of breath, choking or smothering sensations, palpitations or accelerated heart rate, chest pain, sweating, faintness, dizziness, light-headedness, nausea or abdominal distress, depersonalization or derealization, numbness or tingling sensations, hot flashes or chills, trembling or shaking, a fear of dying, or a fear of becoming insane or losing mental control. The frequency and severity of these attacks can result in phobic anxiety and behavior which, in certain instances, can cause the patient to be housebound, or severely restricted in social behavior.

To date, various treatments have been employed for treatment of patients suffering from panic disorders. These treatments include hypnosis and behavior therapies as well as pharmacotherapy. Imipramine hydrochloride and phenelzine sulfate are the most widely prescribed drugs for this indication and, although effective for relief or panic attacks, have undesirable side effects which limit their usefulness. Clinical results with benzodiazepines appear to be variable.

It has now been found that gepirone alleviates some of the symptoms associated with panic disorders. This finding was made by analysis of changes in panic disorder related items contained in standard psychometric instruments. To illustrate, a group of patients suffering from anxiety, but with significant symptoms of panic disorder, were assessed over a 6-week-treatment period using a panic disorder factor which was extracted from the Symptom Check List (SCL-90). The SCL-90 is a self-report symptom inventory, consisting of 90 items, which can be factored into clinical clusters with diagnostic utility; cf: Wilson, et al., *British Journal of Psychiatry*, 147, pp. 400–403 (1985), and references therein. The panic disorder factor of the SCL-90 is the phobic anxiety symptom cluster. Gepirone produced significantly greater improvement in relieving symptoms of panic disorder than did placebo; see FIG. 1.

FIG. 1 shows the time course relationship of the mean patient panic factor score by drug treatment group. The panic factor score is obtained for each patient at weeks 0, 0.5, and 1 through 6 by summing the numerical values assigned to each panic factor symptom item according to severity and/or frequency being experienced. The higher the patient score the greater the degree of illness. As can be seen, there is an improvement in mean score for the gepirone group compared with the placebo group. The comparative improvement for the gepirone group becomes much more evident after week 2 of the study. Currently, studies are being set up to continue investigating gepirone in panic disorder in prospective clinical trials.

The process of the present invention essentially involves administration of gepirone, or a pharmaceutically acceptable acid addition salt thereof, to a patient in need of such treatment. Pharmaceutically acceptable acid addition salts of gepirone and methods of pharmaceutical formulation are described in the patent of Temple, U.S. Pat. No. 4,423,049, which is incorporated herein in its entirety by reference.

Administration of gepirone according to the present invention may be by the parenteral, oral, or rectal routes. The oral route is preferred, however. The clinical dosage range for alleviation of panic disorders is expected to be less than about 100 mg per day, generally in the 20 to 80 mg range and preferable in the range of 30–60 mg per day. Since the dosage should be tailored to the individual patient, the usual practice is to commence with a dose of about 10 mg administered two or three times per day and then to increase the dose every two or three days by 5 mg at each dosage time until the desired response is observed or until the patient exhibits side effects. Single daily dosage may be applicable in some instances.

What is claimed is:

1. A method for alleviation of panic disorders which comprises administering a non-toxic therapeutically effective dose of gepirone or a pharmaceutically acceptable acid addition salt thereof to a patient in need of such treatment.

2. The method of claim 1 wherein gepirone hydrochloride is employed and dosage is by the oral route.

3. The method of claim 1 wherein panic attacks is the specific panic disorder afflicting said patient.

4. The method of claim 1 wherein agoraphobia is the specific panic disorder afflicting said patient.

5. The method of claim 1 wherein phobic anxiety is the specific panic disorder afflicting said patient.

6. The method of claim 2, 3, 4, or 5 wherein said patient is an adult and a daily dose of from about 10 mg to 60 mg is employed.

7. The method of claim 6 wherein said daily dose is divided and administered b.i.d.

8. The method of claim 6 wherein said daily dose is divided and administered t.i.d.

* * * * *